(12) United States Patent
Taylor et al.

(10) Patent No.: US 6,627,450 B1
(45) Date of Patent: Sep. 30, 2003

(54) METHOD OF MEASURING CHLORINE CONTENT IN AQUEOUS SOLUTION

(75) Inventors: Robert M. Taylor, Lansdale; Dianne M. Phelan, Telford, both of PA (US)

(73) Assignee: Severn Trent Water Purifications, Inc., Colmar, PA (US)

( * ) Notice: Subject to any disclaimer, the term of this patent is extended or adjusted under 35 U.S.C. 154(b) by 0 days.

(21) Appl. No.: 09/502,608

(22) Filed: Feb. 11, 2000

(51) Int. Cl.⁷ .................................. G01N 33/00
(52) U.S. Cl. ........................... 436/125; 436/150
(58) Field of Search .................... 422/61, 81; 210/756; 205/789; 436/125

(56) References Cited

U.S. PATENT DOCUMENTS

| | | | |
|---|---|---|---|
| 3,966,413 A | * 6/1976 | Marinenko | 422/81 |
| 4,253,847 A | * 3/1981 | Matson et al. | 205/789.5 |
| 4,322,215 A | * 3/1982 | Huber et al. | 205/778.5 |
| 4,487,262 A | 12/1984 | Venkatesan et al. | |
| 4,609,594 A | 9/1986 | Odashima et al. | |
| 5,783,149 A | * 7/1998 | Serrat | 422/61 |
| 6,022,480 A | * 2/2000 | Girvan et al. | 210/756 |
| 6,180,412 B1 | * 1/2001 | Kroll | 436/125 |

FOREIGN PATENT DOCUMENTS

| | | |
|---|---|---|
| DE | 37 01 727 A | 8/1988 |
| EP | 0 260 230 A | 3/1988 |

OTHER PUBLICATIONS

George Clifford White, "Handbook of Chlorination and Alternative Disinfectives", Van Nostrand Reinhold, New York; third edition, 1992, p. 842.
Patent Abstracts of Japan, vol. 1996, No. 12, Dec. 26, 1996 & JP 08 211042 (Isomura:KK), Aug. 20, 1996.
Patent Abstracts of Japan, vol. 012, No. 235, Jul. 6, 1988 & JP 63 027745 A (Denki Kagaku Keiki Co. Ltd.), Feb. 5, 1988.
Abstract of German Patent No. DE 37 01 727 A, issued Aug. 4, 1988.

* cited by examiner

Primary Examiner—Jeffrey Snay
Assistant Examiner—Samuel Siefke
(74) Attorney, Agent, or Firm—Howson and Howson

(57) ABSTRACT

Methods of measuring free and total chlorine content in solutions are provided without lowering the pH of the solution to the acid range by modifying a solution containing chlorine and water to contain a proton donating compound and electrochemically measuring the concentration of the chlorine in the solution. An additional potassium iodide reagent is added when total chlorine content is measured. Stable aqueous reagent solutions useful in automated chlorine analyzers which contain sodium bicarbonate, a base, and water or borax, water, and acid are also described. Finally, apparatuses for detecting the level of chlorine in water samples utilizing an automated chlorine detector, a cartridge having a solid proton donating compound, and optionally a standpipe are discussed.

12 Claims, 2 Drawing Sheets

METHOD OF MEASURING CHLORINE CONTENT IN AQUEOUS SOLUTION

FIELD OF THE INVENTION

This present invention relates generally to the field of chlorine detection, and specifically relates to a method for measuring chlorine content in automated analyzers.

BACKGROUND OF THE INVENTION

The requirement to provide chlorine analyzers with additional reagents has long been a concern. There exist a number of commercially available residual chlorine analyzers. Current thinking in the industry is that in order to obtain accurate measurements of chlorine levels in water, the chlorine must be in the form of HOCl. Further, it is believed that in order to obtain this electroreducible species, the pH of the sample containing chlorine must be lowered to a pH of about 4.5 to 5, or lower. However, the reagents required to lower the sample pH have several undesirable side-effects. In applications where no drain is available, the measured sample is often discharged onto the ground, which can result in a buildup of a reagent which is often a nutrient and consequentially facilitates a large biological growth. The nutritive nature of the buffers used to date also gives rise to biological growth in the analyzers, potentially fouling electrodes and clogging portals so that more frequent and costly preventative maintenance is required.

Many of the reagent systems studied are based on organic acids. Some of the most readily available aqueous acid systems require the addition of a weak acid salt to create a buffer in order to stabilize the reagents for shipping and storage. Some of the more commonly used systems include phthalate, succinate, acetate, phenylacetate, citrate, phosphate, oxylate, and salicylate. All of these are believed to be biological nutrients, and as such, may cause problems in the growth and contamination of feed lines and storage containers. Some of the less common systems include amine-based buffers derived from substituted glycines and taurines. Taurine based buffers are often substituted for borate buffers in biological systems. Although they are reported to be resistant to enzymatic and non-enzymatic degradation, the organic nature of the compound still makes these acids a probable biological nutrient.

There is a large interest in lessening the disposal problem and reducing or eliminating the nutrient nature of the added reagent to the chlorine analyzer. A variety of different buffers have been utilized, such as phosphates, but none have been found to be generally acceptable. Alternatives have been considered, including operating the chlorine analyzer without buffers or using different buffers. If no reagent is used, however, serious measurement errors can result.

Furthermore, it is important to consider the cost implications of any chemical reagent system that could replace the acetate system. Even the more common organic acids as listed above can be considerably more expensive than the present one.

There remains a need in the art for better methods that allow for chlorine detection at higher pH levels, are cost efficient, and avoid the problems associated with the addition of nutritive reagents to the chlorinated medium.

SUMMARY OF THE INVENTION

In one aspect, the invention provides a method of measuring chlorine content in a solution without lowering the pH of the solution to the acid range by modifying a solution containing chlorine and water to contain a proton donating compound.

In another aspect, the invention provides a method of measuring total chlorine content in an aqueous solution containing a mixture of chloramines without lowering the pH of the solution to the acid range. The method involves adding an iodide salt to an aqueous solution, where the chlorine is present in the aqueous solution as free and combined chlorine, and the steps as described above.

In still another aspect, the invention provides a stable aqueous reagent solution useful in automated chlorine analyzers containing sodium bicarbonate, a base that increases the pH to above about 9.0 without significantly affecting the ability of the sodium bicarbonate to donate protons when mixed with a chlorine solution, and water. A stable aqueous reagent solution containing sodium tetraborate decahydrate, water, and an acid to adjust the pH of the solution to about 6.8 can also be used.

In yet a further aspect, the invention provides an apparatus for detecting the level of chlorine in a water sample. The apparatus includes a cartridge having a solid proton donating compound, an inlet port connected to a water sample supply, and an outlet port in communication with an automated chlorine detector. The inlet and outlet ports of the cartridge are appropriately spaced so that the water sample which flows through the cartridge dissolves the solid proton donating compound. Thereafter, the water sample which contains the dissolved compound is supplied to the automated chlorine detector.

In still another aspect, the invention provides a method of detecting chlorine in an automated chlorine detector using the apparatus as described above.

In another aspect, the invention provides a standpipe apparatus for use in detecting the level of chlorine in a water sample. The standpipe is connected to a supply of water sample and is capable of containing an amount of the sample such that a standpipe water level and a standpipe headspace are defined. The standpipe has an outlet which is adjacent the water lever and which supplies a flow of water sample to a chamber of an automated chlorine detector. The standpipe has another outlet which is spaced below the water level and which feeds a flow of water sample to a cartridge which contains a solid proton dissociating compound and which has a larger volume than the standpipe. The water sample which flows through the cartridge dissolves the compound and is fed into a mixing chamber in the chlorine detector. In addition, the apparatus can include means for adding iodide to the sample water in the standpipe.

In still another aspect, the invention provides a method of detecting chlorine in an automated chlorine detector using the apparatus above.

Other aspects of the invention are described further in the following detailed description of the preferred embodiments thereof

BRIEF DESCRIPTION OF THE DRAWINGS

The foregoing and other objects, features and advantages of the present invention should become apparent from the following description when taken in conjunction with the accompanying drawings, in which.

DETAILED DESCRIPTION OF THE INVENTION

Figure 1:
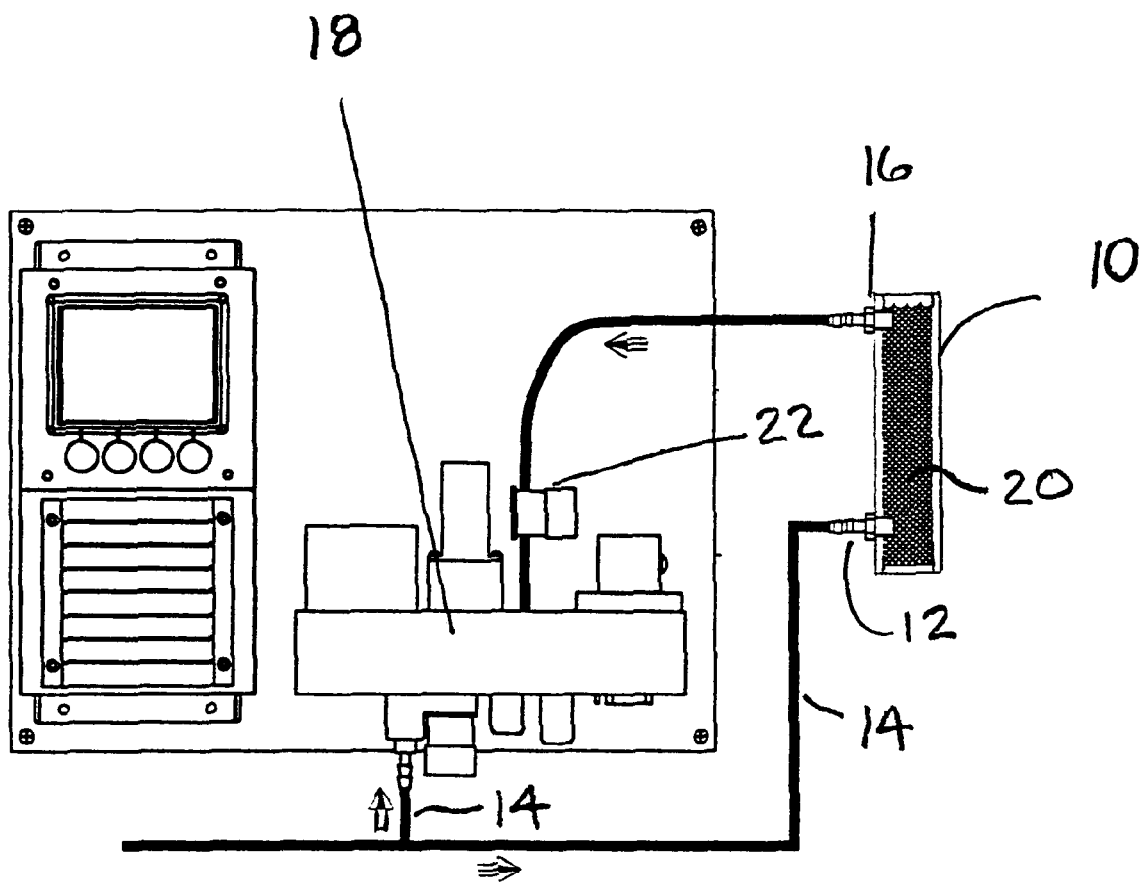
FIG. 1 is a schematic diagram of an elevational view of the cartridge reagent addition system.

The inventors have found, that in contrast to that which is conventionally believed in the art, an aqueous solution containing chlorine does not have to be adjusted into the acid pH range to provide chlorine in the form of HOCl for measurement of the chlorine in an automated detector. Rather, the inventors have found that the only requirement is that there be an excess of protons, which allows chlorine to be measured regardless of its form. Thus, the invention avoids the problems associated with the addition of pH-lowering reagents into a chlorine detection system. The invention also avoids the problems associated with stability, toxicity, storage, and shipping of such pH-lowering reagents.

Thus, the present invention provides novel methods, stable reagent solutions, and devices for chlorine detection in aqueous solutions without lowering pH levels. The advantages of each of these embodiments of the invention are described in more detail below.

I. The Methods of the Invention

The invention provides a method of measuring chlorine content in a solution without lowering the pH of the solution to the acid range by modifying a solution containing chlorine and water to contain a proton donating compound and measuring the concentration of chlorine in the solution. The solution can be modified by adding an exogenous source of a proton donating compound and/or generating or adding a proton species in the aqueous chlorine solution electrochemically.

As used herein, the term "chlorine solution" is meant to describe any solution that contains chlorine. The solutions are typically aqueous, with water being the major component in the solution, and wherein small amounts of other compounds may be present. The chlorine solutions may contain minuscule amounts of chlorine ranging from, but not necessarily limited to, 0 to about 0.07 parts per million (ppm) of chlorine, and more preferably up to about 1 ppm, such as may be obtained from tap water systems available to the public. Alternatively the method of the invention may be applied to water samples containing more concentrated amounts of chlorine, such as those obtained from water treatment facilities. Such concentrations of chlorine may be in the range of about 1 to about 300 ppm or higher. Typically, such chlorine concentrations may be found in amounts from about 1 to about 2 ppm, about 5 to about 20 ppm, about 30 ppm to about 60 ppm, depending upon the source of the chlorine solution being tested. The present invention is not limited as to the source of the chlorine solution to be tested.

The term "combined chlorine" as used herein is meant to describe any chemical compound formed by binding between chlorine and molecules other than chlorine, hydrogen, or oxygen. Chlorine can react with many chemical compounds and includes, but is not limited to, amines. The amine(s) may include, but is not limited to, ammonia ($NH_3$), primary ($NH_2R$), secondary ($NHR_2$), and tertiary amines ($NR_3$). The most common amine present in aqueous chlorine solutions is ammonia. When chlorine reacts with an amine, a "chloramine" complex is formed. A variety of chloramines can be formed and include, but are not limited to, $NH_2Cl$, $NHCl_2$, or $NCl_3$. The term "free chlorine" is meant to describe any form of chlorine that is not combined and in a form suitable for analysis in an automated chlorine detector or other suitable system following mixing with a proton donating compound, as defined herein. Non-combined chlorine may include chlorine which is bound to another chlorine atom, hydrogen or oxygen and which convert to $Cl^-$, $HOCl^-$, and $OCl^-$ when mixed with water.

As used herein, a "proton donating compound" is meant to describe any chemical compound that has the ability to release protons ($H^+$) upon demand. In one desirable embodiment, such proton donating compounds are added from an exogenous source to a sample of a chlorine solution to be measured for chlorine content. In this circumstance, these proton donating compounds are referred to as reagents. Alternatively, a proton may be generated upon application of electrical current to water.

A. Free Chlorine

Thus, in one aspect, the invention involves mixing a sample of a chlorine solution with a reagent of the invention and measuring chlorine content using conventional detection systems. In one desirable embodiment, the sample is mixed with a reagent which contains a chemical source of the proton donating compound.

Desirably, where the reagent contains a chemical source of the proton donating compound, the compound has a relatively high solubility. The hydrogen ion requirement is directly proportional to the chlorine concentration in the sample, such that electroreduction of one ppm of $Cl_2$ requires 14 $\mu$M of $H^+$. If the chlorine is in the $OCl^-$ form, another 14 $\mu$moles of $H^+$ are needed to covert it to HOCl. Though it is possible to add a less concentrated reagent at a high rate, a dilution of 1000:1 (sample:reagent) or higher is optimal, since in minimizes measurement errors due to dilution. Preferably, the available proton concentration in any reagent should meet or exceed 50 mM for each ppm of chlorine measured. However, the invention and selection of the chemical proton donating reagent is not so limited. Most suitably, the proton donating reagent is environmentally inert, i.e., it is neither a nutrient nor has toxic effects on organisms. Additionally, a reagent having chemical stability is preferred.

Many such chemical compounds are known to those of skill in the art. Particularly desirable are non-nutritive proton donating compounds such as carbonate and borate salts. A variety of compounds that fulfill these requirements are available and include, but are not limited to, bicarbonate and borate salts, of which lithium, potassium or sodium bicarbonate and sodium tetraborate decahydrate (Borax) are the most common. Sodium bicarbonate and tetraborate decahydrate are the most economical and are currently the preferred proton donating compounds for use in the invention. However, other suitable compounds may be readily selected from among other known proton donating compounds including, without limitation, weak acids, including those derived from acetate and phosphate, and their corresponding salts.

Advantageously, many of the reagents useful in the invention can be shipped as solids and are readily dissolved for use in measuring chlorine content. Optionally, these reagents may be added in solution form, i.e., the reagents are pre-dissolved in water. Examples of preferred solutions are discussed in more detail below. Alternatively, the solid reagents may be mixed directly with a sample from the chlorine solution. One of skill in the art can readily determine the amount of reagent which is required for measurement of chlorine content in a given sample, taking into consideration the proton donating compound selected, the source of the water sample, and the like.

For example, in one preferred embodiment, the proton donating reagent utilized is sodium bicarbonate. Typically, the amount required to obtain accurate measurement of the chlorine content of a sample is in the amount of sodium bicarbonate contained in a solution containing from 0.07 to 0.8, or preferably, 0.02 to 0.5 molar. However, due to the low cost of the reagent, an excess of the solid, e.g., solutions ranging from from 0.3 molar to 1 molar sodium bicarbonate, may be readily utilized. Similarly, the concentrations for other suitable reagents may be readily determined, and where desired, used in excess of the concentration required for measurement.

Upon the addition of the reagent to the chlorine solution, the pH of the solution may change. Typically, when the reagent is added to the chlorine solution, the pH rises to the basic range. Generally, the pH of the solution rises to about 8.8 when sodium bicarbonate is added and 8.7 when borax is used. Optionally, additional compounds may added to the solution which may serve to adjust the pH or function as buffers. Such additional compounds may include, but are not limited to, acids, bases, and salts.

The addition of an exogenous proton donating compound is not the only method of modifying an aqueous chlorine solution to contain protons. Proton species may be generated electrochemically using standard electrochemical instruments, reagents, and electrodes. The electrochemical generation of protons can be accomplished in an electrolytic cell via oxidation of water. Two or more electrodes may be utilized, but two electrodes are preferred and can be selected from any of a number of inert, conductive materials, including, but not limited to, gold (Au), platinum (Pt), silver (Ag), graphite, vitreous carbon, or oxide-coated "dimensionally stable" metals. When two electrodes, one as a cathode and one as the anode, are utilized, they are typically placed in the water sample and a current passed between the electrodes. Upon doing so, the water is oxidized to produce free protons. These proton species may be generated directly in the aqueous chlorine solution, but are preferably generally separately in a water sample and thereafter added to the chlorine solution to be analyzed.

The reagent may be added or mixed with the water sample prior to being delivered to the analyzer. Alternatively, using conventional analyzers, the reagent and water sample may be separately delivered to the analyzer, thereafter proceed to a mixing chamber, and after such mixing the chlorine levels may be measured electrochemically. Regardless of how the sample is modified to contain a proton donating species, the measurement of chlorine content after the addition or generation of proton donating compounds in the aqueous chlorine solution is typically accomplished electrochemically. "Electrochemical measurements" involve utilization of two or more, and most typically, two electrodes in which one has a negative potential (cathode) where reduction takes place and one has a positive potential (anode) where oxidation takes place. A variety of electrodes can be utilized and are well known to those of skill in the art and include any number of inert, conductive materials, such as those identified above, and additionally, copper may be used as an anode. The electrode(s) are typically placed in the sample to be measured and a small current is passed between the electrodes using standard instruments. Actual electrochemical measurements of the chlorine in the aqueous solution can be accomplished using a variety of electrochemical instruments well known to those skilled in the art. These instruments include, but are not limited to, models available from Capital Controls Company (Colmar, Pa.), such as 1874, 1770, 1870E, CL1000, CL500, and models available from Wallace & Tiernan (e.g., Micro/2000), among others.

B. Combined Chlorine

As described above, the method of the invention may be readily performed by a simple step of mixing a proton donating compound with a sample from a chlorine solution where the chlorine is not in combined form. However, the invention is readily adapted to detection of chlorine levels in samples of chlorine solutions containing combined chlorine. In this aspect of the method of the invention, the combined chlorine is reacted in order to permit measurement of total chlorine content in a sample. This may be performed by adding an oxidizable reagent to the sample. Such an oxidizable reagent reacts with the bound chlorine and thereby disrupts such a combined chlorine. Typically, the combined chlorine complex is a chloramine and the oxidizable reagent is an iodide salt. The iodide salt can be selected from, but is not limited to potassium, lithium and sodium iodide. Currently, potassium iodide is preferred. Other suitable oxidizable reagents may be readily selected by one of skill in the art, taking into consideration the type of chlorine complex and the proton donating compound to be used.

Thus, the method involves adding to a complexed chlorine-containing water sample an oxidizable reagent (e.g., an iodide salt) to react with the combined chlorine. The oxidizable reagent may be added in solid form directly to the aqueous solution. However, where the oxidizable reagent is an iodide salt, the reagent is preferably added in solution form, due to the high cost of iodide and the relative simplicity of metering a fluid reagent. Suitably, an aqueous iodide salt solution can be purchased from commercial sources or prepared using conventional techniques, e.g., by the addition of crystalline potassium iodide to water and mixing. Mixing is achieved by sample flowing through the reagent or, where necessary or desired, by mechanical means. Typically, potassium iodide is added in an amount in the range of 5 $\mu$g to 15 $\mu$g per ppm $Cl_2$ per mL sample. From this range, one of skill in the art can readily calculate comparable amounts of other iodide salts useful in the method of the invention.

Optionally, the oxidizable reagent is incubated with the sample for a pre-selected period of time in order to permit the reagent to react with the combined chlorine. Where the oxidizable reagent is the iodide salt solution, the oxidizable reagent is added to the aqueous chlorine solution and incubated for about 2 minutes. However, this incubation period may be adjusted by one of skill in the art to longer or shorter periods, taking into consideration such factors as the oxidizable reagent selected, whether the reagent is added to the sample in solid or solution form, and convenience. Optionally, the flow of the sample into the analyzer may be interrupted to accommodate any incubation period for the iodide oxidation.

Typically, the sample will be mixed with the oxidizable reagent and optionally subjected to the incubation period prior to addition or generation of proton donating compounds to the sample. However, this is not a limitation of the present invention and one may readily add the oxidizable reagent to the reagent containing the proton donating compounds. Thereafter, the total chlorine content may be measured as described above.

Alternatively, combined chlorine in the sample can be measured indirectly. More particularly, free chlorine in a sample may be measured by the method of the invention described in part A above. Then, in a separate reaction, the oxidizable reagent may be added to the sample and the amount of previously combined chlorine may be determined indirectly through detection of oxidation of iodide ($I^-$) to iodine ($I_2$), or triiodide ($I_3^-$). The electro-reduction of iodine gives a signal current proportional to the total chlorine (i.e., the previously combined and the free chlorine) in the sample. Thus, the combined chlorine in the sample may be measured by subtracting the amount of total chlorine from the amount of fee chlorine.

Preferably, any such interruption in flow of sample is interrupted simultaneously with interruption of reagent, to avoid the need for re-equilibriation. However, the flow of the oxidizable reagent (iodide) aloe may be interrupted.

III. Reagent Solutions

In another aspect, the invention provides solutions ready to use in the methods and apparatuses of the invention.

In one desirable embodiment, the invention provides a stable aqueous reagent solution which contains a carbonate compound. Particularly suitable are potassium bicarbonate ($KHCO_3$), which has a concentration of saturation of about 3 M at room temperature and sodium bicarbonate ($NaHCO_3$), which has a concentration of saturation of about 1 M at room temperature. The inventors have found that, in solution, bicarbonate reagents tend to generate carbon dioxide (outgas) slightly with time. This can result in outgassing of the solution, creating bubbles and an increased pressure in the reagent delivery system. The inventors have been able to overcome this complication by the addition of other reagents to bicarbonate solutions that prevent formation of carbon dioxide. Specifically, a base is added to a solution containing bicarbonate which increases the pH to the range of about 8.8 to about 10.33. Preferably, saturated bicarbonate solutions are at a pH of about 9. A variety of bases may be utilized for this purpose and may include, but are not limited to, sodium hydroxide, potassium hydroxide, lithium hydroxide, and magnesium hydroxide, of which sodium hydroxide is preferred. The bicarbonate solution may be present in any concentration, but saturated solutions at room temperature are preferable and have obtained excellent results.

In another desirable embodiment, the stable aqueous reagent solution contains a borate-based reagent, which was optimized to achieve the highest level of $H^+$ ion availability in the sample. In order to maximize the dilution ratio, the concentration of the compound must be as high as possible. In one example, the salt used was sodium tetraborate decahydrate ($Na_2B_4O_7 \cdot 10H_2O$), which is readily available as "Borax". This compound is also considered a "self-buffer" as it dissociates to form an equimolar concentration of metaboric acid ($HBO_2$) and metaborate ion ($BO_2^-$). In order to improve an unsatisfactory solubility of borax, a stable aqueous reagent solution was formed which provided a more than fourfold increase in total borate concentration at ambient temperatures. This solution is produced by adding water and sufficient acid to adjust the pH of the solution to a point which complexes the borate, but prevents the precipitation of boric acid. The optimum pH has been determined to be about 6.8. A variety of acids may be utilized for this purpose and may include, but are not limited to, hydrochloric acid and sulfuric acid, of which hydrochloric acid is preferred. Only minimal amounts of acid are necessary in order for borax to dissolve and a pH of about 6.8 to be obtained. For example, 540 g of $Na_2B_4O_7 \cdot 10H_2O$ was added to 3 liters of deionized water, and as the solid dissolved, 5 N HCl was added to reduce the pH to 6.8. The formulation of borax at this pH has been found to provide advantages in both stability and dissolution of the borax. Upon addition of the borax reagent solution to a sample from a chlorine solution, a pH in the basic region is obtained, e.g., 8.7.

These solutions are useful in a variety of conventional devices for detecting chlorine, as discussed below. Such solutions may be formulated as described above and bottled in a suitable container, such as are known in the art. Typically, such reagent solutions are bottled in 2 liter containers, as are used for feeding conventional chlorine analyzers. Alternatively, the invention provides a unique reagent delivery system. This system is useful with pre-mixed reagent solutions, or for use when a premixed solution is not convenient, e.g., when the samples contain high levels of chlorine.

IV. Devices for Detecting Chlorine

A. Cartridge Reagent System

Advantageously, the method of the invention permits the use of solid reagents which are stable, inexpensive, and readily dissolved in water. Thus, the invention can be performed using a cartridge which is packed with a solid proton donating compound, e.g., sodium bicarbonate, and through which a water sample can pass. Suitably, the cartridge is an elongate receptacle, e.g., a tube or canister, which contains an inlet port and an outlet port located at opposing ends of the receptacle through which sample water passes and dissolves the solid proton donating compound. Preferably, the sample passes through the cartridge at a rate which allows it to become at least nearly saturated, about 50% to 100%, and desirably at least about 80% saturated. However, lower saturation concentrations may be used, as desired. Thus, when the sample water exits the cartridge, the sample water contains the dissolved compound therein.

The outlet port of the cartridge delivers the water and dissolved compound to an automated chlorine detector. Suitably, a water sample is delivered to the cartridge through the inlet port and the water is permitted to pass through the cartridge, thereby dissolving and becoming saturated with the proton donating compound. After passing through the cartridge, the saturated water sample is delivered to the automated chlorine detector for measurement. The elongated cartridge may be horizontally disposed, or more preferably, vertically disposed.

In one embodiment (with reference to FIG. 1), the elongated cartridge 10 has an inlet port 12 which is connected to a supply of the chlorine water sample via a feed tube 14 and an outlet port 16 which is connected to an automated chlorine detector 18. Preferably, the inlet port 12 is located adjacent a lower end of the cartridge 10, and the outlet port 16 is located adjacent an upper end of the cartridge 10. Thus, the spacing between the ports 12 and 16 ensure that the sample water received by the cartridge 10 via the inlet port 12 flows through a majority of the length of the elongated cartridge 10 before exiting through the outlet port 16 and into the automated chlorine detector 18. The automated chlorine detector 18 is also directly supplied with water sample via feed tube 14.

The cartridge 10 contains a proton donating compound 20 which can be selected from, but is not limited to bicarbonate or borate salts. The water flowing through the length of the cartridge 10 dissolves and becomes saturated with the compound 20. Thus, the automated chlorine detector 18 is supplied via the cartridge 10 with a water sample having the proton donating compound 20 dissolved therein. Optionally, the water sample with the dissolved proton donating compound 20 may be subjected to mixing prior to measurement in the automated detector 18.

Preferably, a solenoid valve 22 is utilized to control the flow of the saturated sample water from the cartridge 10 to the detector 18. This solenoid valve 22 also functions to limit flow through the cartridge. To this end, the solenoid valve 22 is connected directly in the path of flow of the water sample between the outlet port 16 of the cartridge 10 and the detector 18. The solenoid valve 22, and therefore the flow of reagent into the detector 18, is controlled by the detector 18. Optionally, the water sample may be supplied to the cartridge via a pump (not shown).

B. "Standpipe" Reagent Addition System

Figure 2:
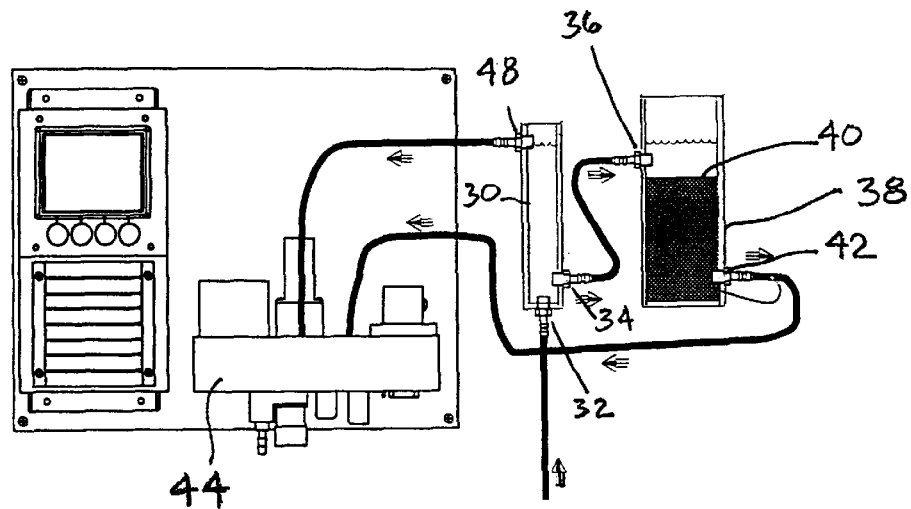
FIG. 2 is a schematic diagram of an elevational view of a "standpipe" reagent addition system.
Figure 3:
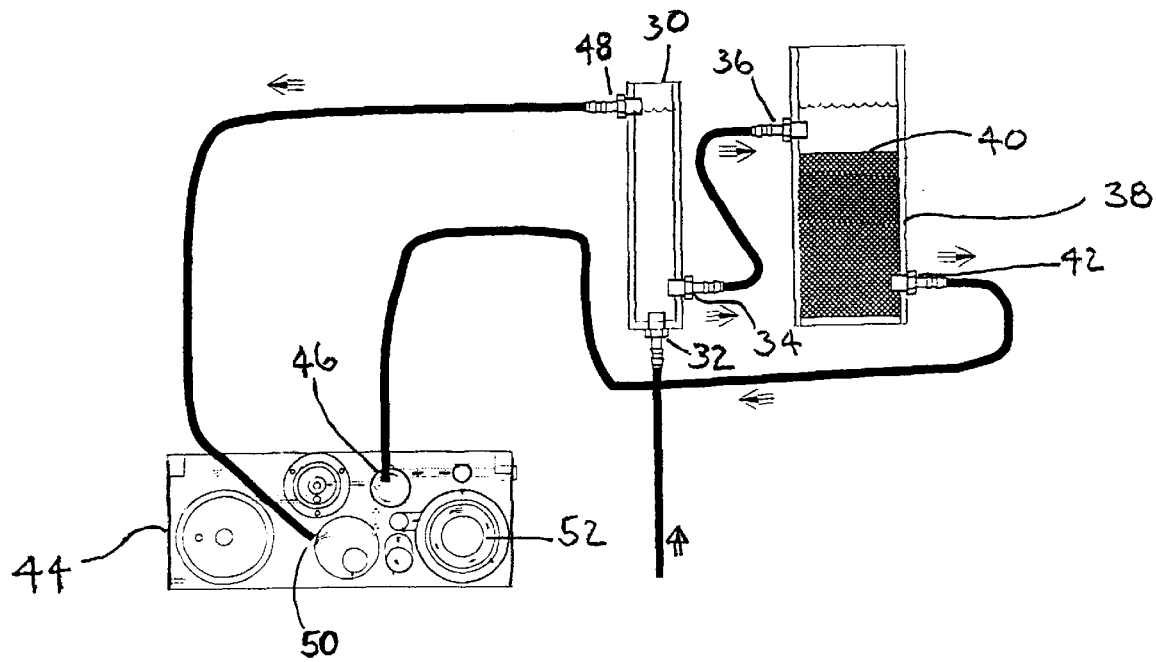
FIG. 3 is a schematic diagram of a plan view of the "standpipe" reagent addition system.

Another embodiment of this invention provides an apparatus including an automated chlorine detector, a standpipe, and a cartridge containing a solid proton donating compound. For purposes of illustration, reference may be made to FIGS. 2 and 3. However, the invention is not so limited.

The standpipe is a receptacle containing an inlet port through which sample water is received and at least two outlet ports. One of the standpipe outlet ports is connected to the cartridge and one of the standpipe outlet ports delivers sample water directly to the analyzer. The standpipe has a first outlet port located well below the water sample level in the standpipe and a second outlet port which is located at, or near, the water sample level. The second outlet port is in fluid communication with the sample inlet chamber of the automated chlorine detector, while the first outlet port supplies sample water to the cartridge.

The cartridge contains a solid proton donating compound (as defined above) and has an inlet port which is in fluid communication with the first outlet port of the standpipe. The cartridge also has an outlet port which is spaced from the inlet port and which is in fluid communication with the mixing chamber of the automated chlorine detector. Preferably, the inlet and outlet ports of the cartridge are located at opposite ends of the elongate cartridge, and the cartridge has a greater volume than the standpipe.

The inlet port of the standpipe is connected to a supply of water sample which fills the standpipe to a predetermined level, thus defining a head space in the standpipe. The sample flow into the standpipe is controlled by a valve which controls flow at a rate sufficient for the analyzer. For example, in the case of analyzers manufactured by Capital Controls, the valve is opened until there is enough flow that water flows over the built-in weir. When water flows out of the weir, there is established a water head which, given the internal resistance to flow with the analyzer, assures the proper sample flow through the analyzer. The operator adjusts the sample flow valve just as if the sample were flowing directly to the analyzer and not first through the standpipe.

Typically, the height of the standpipe, and its relationship to the height of the cartridge, controls the delivery of the proton donating compound to the analyzer. For instance, the standpipe and the cartridge may be elevated, as compared to the fluid level in the mixing chamber of the analyzer, when it is desirable to increase the flow of sample to the analyzer. In the alternative, the elevation of the cartridge and the standpipe may be adjusted downwardly relevant to the analyzer to decrease the flow of reagent to the analyzer. Typically, a suitable flow rate of reagent to the analyzer is achieved when the level of the head space in the cartridge is equal to, or slightly below, the level of the head space in the standpipe. Thus, this embodiment of the invention avoids the need for a solenoid valve, or like device, to control the rate of flow into the automated chlorine analyzer/detector.

Optionally, the device can include a tube (not shown) which feeds into the inlet port of the standpipe and permits the addition of an oxidizable reagent (e.g. iodide) to the sample water entering the standpipe. The size (i.e., width or diameter) of the standpipe may be adjusted as desired so that the sample which is introduced into the inlet port of the standpipe does not exit the standpipe through the exit port to the analyzer within the amount of time required to incubate the oxidizable reagent with the sample. For example, where the oxidizable reagent is iodide, the size of the standpipe is modified such that an entering sample does not reach the exit port for a period of at least about 2 minutes. It is well within the skill of one in the art to determine the size of the standpipe required to ensure the appropriate incubation time.

In one suitable embodiment, the water sample flows into a standpipe 30 via an inlet port 32 located in the base of the elongate standpipe 30. A first outlet port 34 is provided adjacent the base of the standpipe 30 and provides a path of flow of sample water from adjacent the base of the standpipe 30 to an inlet port 36 located adjacent the upper end of a cartridge 38. The pressure of the water located in the standpipe 30 forces the flow of water into the cartridge 38.

The water sample entering the cartridge 38 flows downwardly through a solid proton donating reagent 40 located in the cartridge 38 and becomes saturated therewith prior to exiting the cartridge 38 through an exit port 42 which is located at the lower end of the cartridge 38 and which is in fluid communication with a mixing chamber 46 of the analyzer 44. At the same time, the remaining sample water entering through the inlet port 32 of the standpipe 30 increases the water level in the standpipe until the water level reaches an outlet port 48 located adjacent the upper end of the standpipe 30. The standpipe outlet port 48 is in direct fluid communication with an inlet chamber 50 in the analyzer 44 to supply the analyzer 44 with sample water. Thus, the sample water exiting the standpipe 30 and the reagent solution exiting the cartridge 38 are delivered to separate chambers within the analyzer 44, are mixed, and are then delivered to an analyzer cell 52. Optionally, the sample water exiting the standpipe 30 and the reagent solution exiting the cartridge 38 can be delivered directly to an analyzer cell 52 of the automated chlorine analyzer 44.

Thus, the devices of the invention are useful for performing the novel methods of the invention. However, these devices are readily adapted for use with a variety of other detection methods known in the art, as will be apparent to one of skill in the art.

V. EXAMPLES

The following examples illustrate the various aspects of the invention, including the various proton donating reagents. These examples do not limit the scope of the invention, which is embodied in the appended claims.

Example 1—Comparison of Borate, Phosphate and Acetate Reagents Over Varying pH Conditions Example 1 demonstrates the dependence of chlorine detection via amperimetric current on the availability of protons, as opposed to pH. Specifically, this example illustrates that electrochemical chlorine measurements can be made at pH values over 5.5. The reagent systems used in the past, acetate and phosphate buffers which lower the pH to the acid range (about 4.0–4.5), do not allow for measurements to made at higher pH values. The versatility of borax at low and high pH values is further illustrated.

A. Electrochemical Chlorine Detectors

Chlorine detection was accomplished via electrochemical cyclic voltammetry using a Model 273A Polarographic Analyzer with Model 270 Research Software Version 4.23 (Princeton Applied Research, Inc.).

Cyclic voltammetry on two types of analyzers, CL1000 and CL500 [Capital Controls], were run in parallel. All tests were conducted with the analyzers operating in their default mode, with the conditions found in Table 1.

TABLE 1

|  | CL1000 | CL500 |
| --- | --- | --- |
| offset current | 0.0 μamps | 0.0 μamps |
| sensitivity | 35 μamps/ppm $Cl_2$ | 35 μamps/ppm $Cl_2$ |
| default bias voltage | −0.1 volts* | 0 volts[x] |

*the gold cathode is 0.1 volt negative of the reference electrode potential
[x]the gold and copper electrodes were maintained at the same potential The CL500 analyzers employ a conventional gold cathode and copper anode with a zero potential between them in a two-electrode cell. The CL1000 analyzers employ a silver/silver chloride reference electrode along with the gold cathode and copper anode in a three-electrode configuration.

B. DPD Measurements

Chlorine concentrations were measured with a Hach DR 20000 spectrophotometer and DPD Permachem free chlorine reagent (#14070-99). DPD (n,n-diphenylene diamine) measurements in the solutions were made to determine the true concentration of both free and combined forms of chlorine in the aqueous solutions and were compared to the results obtained from the CL500 and CL1000 analyzer readings to make sure that the CL1000/CL500 measurements were correct. It should be noted that only a single DPD measurement was made for each chlorine concentration of interest. Errors of at least several percent are to be expected. When accuracy verification is later undertaken, repeated DPD tests and/or amperometric titrations [using, for example, a Fisher & Porter model 17T2 titrator] are required to obtain a reference method as accurate as the amperometric analyzers being tested. Data was recorded on strip-chart recorders (Yokogawa model 731143 and Graphtec model WR 7800) and digitally using National Instruments Corp. "Measure 2.0" and Microsoft "Excel" software.

C. Reagents

1. Acetate Buffer

The standard acetate buffer was obtained from Capital Controls, Colmar (CCC #a-1806), which contained approximately 7.89 M acetic acid and 2.95 M sodium acetate to give a final pH of 4.5.

2. Phosphate Reagent

The phosphate reagent was produced by adding approximately 0.25 g of mono-H sodium orthophosphate [$Na_2HPO_4.7H_2O$, Fisher Scientific, ACS grade] and approximately 0.1 mL of phosphoric acid to 1000 mL of water to provide an phosphate concentration of approximately 0.001 M.

3. Borate Reagent

The borate reagent was produced by adding 540 g of $Na_2B_4O_7.10H_2O$ (Twenty Mule Team brand Borax) to 3 liters of deionized water to provide a borate concentration of 0.001 M in the forms [$H_2BO_4$]$^-$ and [$HBO_4$]$^{-2}$. The final pH was adjusted to about 6.8 by adding approximately 350 mL of 5 N HCl to the borate solution. The added acid increased the solubility of the borax. Due to some idiosyncracies of borate chemistry, the resultant chlorine sample, after the addition of the buffer solution had a pH of 8.7.

4. Potassium Bicarbonate Reagent

A bicarbonate reagent was produced by adding 900 g of potassium bicarbonate [Fisher Scientific, ACS grade] to 3.0 liters of deionized water to provide a near-saturated bicarbonate concentration of 3 M at room temperature.

5. Sodium Bicarbonate Reagent

A bicarbonate reagent was employed by adding 270 g of sodium bicarbonate [$NaHCO_3$, Arm & Hammer brand, USP grade] to 3.0 liters of deionized water to provide a near-saturated bicarbonate concentration of about 1 M at room temperature.

D. Chlorine Solutions

1. Background Chlorine Sample

Background sample water of a very low chlorine content was made by passing chlorinated tap water through a carbon filter. The resultant water had about 0 to about 0.05 ppm chlorine content.

2. Test Chlorine Sample

Test sample water of a larger chlorine content was prepared by adding 20 mL of sodium hypochlorite (5% NaOCl, CLOROX brand bleach) to 215 liters of deionized water to obtain a 0.347 M solution.

E. Cyclic Voltammogram Measurements

Cyclic voltammograms were obtained with chlorine present. The scans were carried out at varying slow scan rates, which was essential to simulate the steady state cell operation typical of amperometric analyzers. The default setting for buffer addition was 1 pulse every about 11.5 seconds, resulting in an about 80 μL/min flow. The sample flow through the instrument was typically about 125 ml/min.

For each analyzer tested, subtracting the cyclic voltammogram obtained from a background chlorine sample from a test sample chlorine sample gives rise to the current-voltage curve of the reduction of chlorine under the test conditions employed.

F. Calibration Curves

Calibration curves for the analyzers were obtained to determine the presence of background current and the sensitivity of each analyzer. Typically, these curves are the measured output of the analyzer (current, typically in microamps) plotted versus the DPD measured value. The scatter relates to precision, the stability of the offset (if any) at zero limits the low level of measurement which can be obtained, and the linearity is verified (the instruments presume that the current increases linearly).

G. Procedure

To compare buffering capacities, three chlorine samples were buffered with the borate and phosphate reagent solutions described above. A blank solution, to which no additional buffer or reagent was added to the water, was also utilized.

The sample pH was titrated upward with 1 N sodium hydroxide, slowly, drop wise and down with 5 N hydrochloric acid over the pH range 4.5 to 9.0.

H. Results

Results indicate that the amperimetric signal for the phosphate and borate buffered water samples remained at a high and near constant value as the pH was raised to about 9. As the pH was further increased above 9.0, the amperimetric currents for the phosphate and acetate solutions rapidly decayed, while the current for the borate solutions remained the same.

The amperometric signal for the unbuffered water sample however began to fall at about a pH of 6.0. As the pH was raised over 9.2, most of the signal was lost. Coincidentally, the amount of chlorine present in the HOCl form rapidly rises as the pH is increased from about 0 to about 3, is maintained at a pH of about 3 to about 5.5, and decays along with the signal to about 0 for the unbuffered solution over pH values of about 5.5 to about 9.5. However, while the amount of chlorine in the HOCl form decayed at pH values above about 5.5, the signal for the phosphate and borate solutions remained approximately steady up to about a pH of 9.0, where the phosphate and acetate solution signals began to fail. Above the pH value of about 9.0, the signal for the borate solution continued to remain steady while the HOCl form had decayed to 0.

Chlorine detection of the samples buffered using phosphate and borate systems clearly does not depend on the pH of the solution being below 5.0, as is generally understood by those skilled in the art. Instead, it appears that in order for chlorine measurements to be made, sufficient amounts of protons must be present to convert the OCl⁻ to the electroreducible HOCl species. This was accomplished in Example 1 by adding phosphate or borate buffers, which all weakly donate protons to the chlorine sample. These results showed, as indicated above, that all of these buffers were successful in aiding chlorine detection up to about 9.0, but in these test conditions only the borate reagent was successful at pH values over 9.0. In addition, because the borate reagent has no nutritive properties, biological growth in the analyzer would not occur.

Example 2—Measurement of Chlorine in an Aqueous Solution Using Acetate Reagent The acetate buffer was tested to obtain a performance baseline against which other reagent formulations are compared. Example 2 describes the measurement of free chlorine in an aqueous solution using the acetate buffer at a pH value of about 4.5.

A. Procedure

Three analyzers, two CL1000s (Units #1 and 4) and one CL500 (Unit #6) instrument, were run using the standard acetate buffer as described in Example 1. The resultant formulation was obtained by adding a 7.89 M acetic acid solution to a 2.95 M sodium acetate solution to give a final pH of 4.5. Aqueous chlorine solutions with negligible amounts of chlorine, 0.03, 0.05, and 0.03 ppm, as the background samples, and solutions with 1.21, 1.5, and 1.8 ppm of chlorine, as the test samples, were prepared as described in Example 1.

B. Calibration Curves

All three analyzer units showed linear dependence of the DPD on chlorine concentration. There is also a moderately small background current in each case, and the sensitivity of each analyzer approximates the expected 35 $\mu$amps/ppm. The CL500 had the lowest background current and the lowest sensitivity, albeit by only a small margin. The sensitivities of the three units were 35 $\mu$amps/ppm (Unit #6), 40 $\mu$amps/ppm (Unit #1), and 47 $\mu$amps/ppm (Unit #4). These values are good, being near or slightly above the expected 35 $\mu$amps/ppm.

C. Results

Current/voltage curves were obtained from a single cyclic voltammogram with chlorine present (test sample) and in its absence (background sample). All of the units using the acetate buffer behaved similarly, with the scans of each indicating that a bias voltage of +100 mV would be preferred to the −100 mV default value. The more positive bias would reduce the background current, i.e. the offset current, while keeping the sensitivity virtually unchanged.

Example 3—Measurement of Chlorine in an Aqueous Solution Using Borate Reagent Example 3 describes the measurement of free chlorine in an aqueous solution using a borate reagent at a pH value of about 6.8. This example specifically illustrates that chlorine detection can be accomplished at higher pH values rather than acidic pH values used in current methods of chlorine detection.

A. Procedure

Two analyzers, Unit #2, a CL500, and Unit #5, a CL1000 at −100 mV versus its Ag/AgCl reference electrode, were run using the standard borate reagent as described in Example 1. The resultant formulation was 3 liters of deionized water to which was added 540 grams of $Na_2B_4O_7 \cdot 10H_2O$, and the final pH being adjusted to 6.8 using approximately 350 mL of 5 N HCl.

The pH of the effluent from each analyzer was measured approximately daily; the sample pH after the borate reagent addition was consistently approximately 8.7.

Aqueous chlorine solutions with negligible amounts of chlorine, 0.03 and 0.03 ppm, as the background samples, and solutions with 1.68 and 1.3 ppm of chlorine, as the test samples, were prepared as described in Example 1.

B. Calibration Curves

The calibration curves for the two analyzers using borate reagent (not shown) showed linear dependence of the measured signal current to the chlorine concentration (verified by DPD tests) in both analyzers. The sensitivities of the two analyzers were similar, but less than the 35 $\mu$amps/ppm of chlorine typical of analyzers using acetate buffer. Unit #4 had a sensitivity of 26 $\mu$amps/ppm of chlorine and the sensitivity of Unit #5 was 24 $\mu$amps/ppm.

The difference in the zero offset was due to the different operating potentials of the two analyzers. Unit #2, operating with the gold electrode at the same potential as the copper anode, had very little background current, i.e. the current in the absence of chlorine was nearly zero. The background current of Unit #5 was approximately 56 $\mu$amps, equivalent to 1.6 ppm of chlorine. These results show too high a background current. However, this was found to be due to an error in the software of the manufactured product (the bias was found to be +100 rather than −100 mv as thought). Later research has shown desirable linear curves, with a zero offset.

C. Results

Current/voltage curves were obtained from a single cyclic voltammogram with chlorine present (test sample) and in its absence (background sample).

1. Unit #2—CL500 (Operating With the Gold Electrode at the Same Potential as the Copper Anode)

Current/voltage curves with 0.03 and 1.68 ppm of chlorine present were obtained. The cell was allowed to equilibrate at an applied potential of +500 mV for ten minutes. The potential was then scanned from +500 mV to −400 mV and then back to +600 mV at a scan rate of 0.5 mV/sec.

As was the case for the analyzer using acetate buffer the chlorine reduction wave is apparent, beginning at about +450 mV and reaching a plateau of about +100 mV, indicating that the electrochemistry is as expected.

2. Unit #5—CL1000 (Operating at a Bias of −0.10 Volts Versus its Ag/AgCl Reference Electrode)

Similar cyclic voltammograms were obtained for the CL1000 instrument, also using the borate reagent, for samples containing 1.3 ppm and 0.03 ppm of chlorine. When the curves for these two samples are subtracted form one another, again the chlorine reduction wave is apparent, beginning at approximately +400 mV and reaching a plateau at about +100 mV.

Example 4—Measurement of Chlorine in an Aqueous Solution Using Sodium Bicarbonate Reagent Example 4 describes the measurement of free chlorine in an aqueous solution using the sodium bicarbonate reagent at a pH value of 8.8. This example also illustrates that chlorine detection can be accomplished at higher pH values rather than the acid pH values used in current methods of chlorine detection. However, the importance of using sodium bicarbonate over borax is the fact that sodium bicarbonate is more innocuous and inexpensive than the above described borax reagent.

A. Procedure

Two CL1000 analyzers, Units #3 and 7, were run using the sodium bicarbonate reagent prepared by adding 3.0 liters of deionized water to which was added 270 g of sodium bicarbonate to provide a concentration of 1 M. The sample pH after sodium bicarbonate reagent addition was approximately 8.8. The pH of the effluent from each analyzer was measured approximately daily.

Aqueous chlorine solutions with negligible amounts of chlorine, 0.03 and 0.05 ppm, as the background samples, and solutions with 1.42 and 1.7 ppm of chlorine, as the test samples, were prepared as described in Example 1.

B. Calibration Curves

The calibration curves for the two analyzers using the bicarbonate reagent (not shown) indicate linear dependence of the measured signal current on increasing chlorine concentration as verified by DPD measurement. The sensitivities of the analyzers were very similar, but somewhat less than the 35 $\mu$amps/ppm of chlorine typical of analyzers using acetate buffer. Unit #3 had a sensitivity of 30 $\mu$amps/ppm of chlorine and the sensitivity of Unit #7 was 29 $\mu$amps/ppm.

Each analyzer had a large background current when operated at a −100 mV bias. The background current of Unit #3 was approximately 49 $\mu$amps, equivalent to 1.4 ppm of chlorine. Unit #7 exhibited a background current of approximately 66 $\mu$amps, equivalent to 1.9 ppm of chlorine. As discussed above, this was found to be a result of an error in the software of the manufactured product.

C. Results

Current/voltage curves were obtained from a single cyclic voltammogram with chlorine present (test sample) and in its absence (background sample).

1. Unit #3—CL1000 (operating at a −0.1 volt bias)

Current/voltage curves of samples with 0.03 ppm or 1.42 ppm of chlorine present were obtained. The cell was allowed to equilibrate at an applied potential (gold versus reference electrode) of +500 mV for ten minutes. The potential was then scanned from +500 mV to −400 mV and back to +500 mV at a scan rate of 0.1667 mV/sec. When these current/voltage curves were subtracted from one another, the chlorine reduction wave is apparent, beginning at approximately +500 mV and reaching a plateau at about +100 mV.

2. Unit #6—CL1000 (operating at a −0.1 volt bias)

Similar cyclic voltammograms were obtained for Unit #6, also using the bicarbonate reagent. Current/voltage curves were obtained with 1.7 ppm or 0.05 ppm of chlorine present. This time the cell was equilibrated at +500 mV for 10 minutes, after which the potential was scanned from +500 mV to −400 mV and back at the rate of 0.1667 mV/sec. When the current/voltage curve of 0.05 ppm was subtracted from the curve of 1.7 ppm, again the chlorine reduction wave is apparent, beginning at approximately +400 mV and reaching a plateau at about +100 mV.

Example 5—Long Term Stability of Chlorine Residual Analyzers

The linearity and sensitivity of chlorine residual analyzers CL1000 and CL500s were determined under various test conditions, as was long-term stability. In every test, control analyzers, both in the two and three electrode configurations, were used with acetate reagent as well as with no reagent to confirm baseline performance.

The sample source water (public tap water) had a free chlorine concentration ranging from 200 to 600 ppb (parts per billion), and a negligible level of combined chlorine. The water was passed through a carbon filter that reduced the chlorine content to below 20 ppb. The water was then brought to the desired chlorine level by the addition of bleach. Chlorine concentrations were regularly verified through spectrophotometric DPD (n,n-diphenylene diamine) tests and amperometric titrations. Even though the chlorine concentration was increased to >100 ppm several times during the test period, the majority of the work was done at chlorine concentrations in the 0–5 ppm range.

The study used acetate, borate and sodium and potassium bicarbonate reagents, prepared as described in Example 1C. In all, seven residual chlorine analyzers were run continuously for three months, with virtually no loss in sensitivity, regardless of reagent.

More particularly, there are marked similarities in the results obtained regardless of the reagent used. The linearity and stability of the analyzers were equivalent regardless of the reagent used. The maintenance requirements of analyzers using borate, potassium bicarbonate, or sodium bicarbonate reagents was markedly less than that of those using acetate buffer because there was little or no bio-fouling of the instrument portals or cell. The sensitivity of the units using the borate reagent was typically less than that of units using another reagent; the reason for this was not investigated.

Example 6—The Effect of Reagent Addition Interruption

This example describes the effect on measuring chlorine levels in solutions where the acetate reagent was added less often to the chlorine solution. This example illustrates the advantages, including lower costs and less biological build-up in the analyzer, of using less reagent over a long period of time. This example specifically addresses the use of acetate reagents to measure chlorine concentration at lower pH levels. One of skill in the art would be able to use a carbonate or borate salt in the following example in the place of the acetate reagent.

A. Procedure

CL500 and CL1000 residual chlorine analyzers were utilized. The acetate reagent as described in Example 1 was added to a chlorine water sample. The acetate reagent was prepared by adding a 7.89 M acetic acid solution to a 2.95 M sodium acetate solution to provide a solution with a pH of 4.5. The chlorine water sample was prepared as described in Example 1, where 0.3 ppm of chlorine were present in the sample and was passed through the analyzer continuously with acetate buffer (injected every 6 seconds) until a stable reading was obtained. Then both the sample water flow and the reagent addition were interrupted for a short period to determine the effect.

B. Results

When the acetate reagent addition was interrupted for small increments of time, no decay in the amperometric signal was detected. When the acetate reagent addition was interrupted for large increments of time, a continual decay in the amperometric signal indicative of the residual chlorine concentration was observed. This was similar to what would be expected if no buffer were added. However, about every 100 seconds, when the buffer was added, the signal current would rapidly rise to a value representative of the true chlorine concentration. The recovery of the signal took several seconds, after which the signal returned to a downward drift from the lower value that it had earlier reached. This suggests that the buffer feed could be interrupted for a period of time, perhaps for minutes, after which buffer addition might quickly yield an accurate analysis.

All above-noted published references are incorporated herein by reference. Numerous modification and variations of the present invention are included in the above-identified specification and are expected to be obvious to one of skill in the art. Such modifications and alterations to the methods, solutions, and apparatuses of the present invention are believed to be encompassed in the scope of the claims appended hereto.

What is claimed is:

1. A method of measuring total chlorine content in an aqueous solution comprising the steps of:

(a) adding an iodide salt to an aqueous solution which comprises chlorine and an amine, wherein said chlorine is present in said aqueous solution as free and combined chlorine, and whereby said salt reacts with any chlorine, (b) modifying the aqueous solution to contain a proton donating compound without lowering the pH of said solution to the acid range, (c) measuring the iodine produced by reaction of iodide with chlorine, and (d) determining the total chlorine in said solution indirectly by correlating the measured iodine to the concentration of chlorine in said solution.

2. The method according to claim 1, wherein said aqueous solution of step (a) comprises a mixture of amines.

3. The method according to claim 1, wherein the amine is ammonia.

4. The method according to claim 1, wherein said proton donating compound is a non-nutritive reagent.

5. The method according to claim 4, wherein said proton donating compound is a bicarbonate or borate salt.

6. The method according to claim 5, wherein said bicarbonate salt is sodium bicarbonate.

7. The method according to claim 5, wherein said borate salt is sodium tetraborate decahydrate.

8. The method according to claim 1, wherein the chlorine concentration in said aqueous solution is measured electrochemically.

9. The method according to claim 1, where the combined form of chlorine is selected from $NH_2Cl$, $NHCl_2$, $NCl_3$.

10. The method according to claim 1, wherein said iodide salt is selected from potassium iodide, lithium iodide, and sodium iodide.

11. The method according to claim 1, wherein the pH of said solution is about 5.5 to about 10.

12. The method according to claim 1, wherein the pH of said solution is about 7.

* * * * *